(12) United States Patent
Whitlock

(10) Patent No.: US 8,985,033 B1
(45) Date of Patent: Mar. 24, 2015

(54) ADJUSTABLE TATTOO TABLE

(71) Applicant: James Whitlock, Clearwater, FL (US)

(72) Inventor: James Whitlock, Clearwater, FL (US)

( * ) Notice: Subject to any disclaimer, the term of this patent is extended or adjusted under 35 U.S.C. 154(b) by 0 days.

(21) Appl. No.: 14/192,021

(22) Filed: Feb. 27, 2014

(51) Int. Cl.
*A47B 5/00* (2006.01)
*A47B 37/00* (2006.01)
*A47B 13/00* (2006.01)
*A47B 5/02* (2006.01)
*A47B 9/00* (2006.01)

(52) U.S. Cl.
CPC ............... *A47B 37/00* (2013.01); *A47B 13/00* (2013.01); *A47B 5/02* (2013.01); *A47B 9/00* (2013.01)
USPC ............................................ 108/152; 108/49

(58) Field of Classification Search
USPC .................... 108/152, 49, 25, 90, 59
See application file for complete search history.

(56) References Cited

U.S. PATENT DOCUMENTS

| | | | | |
|---|---|---|---|---|
| 1,046,479 A * | 12/1912 | McPherson | ...................... | 108/49 |
| 1,232,757 A * | 7/1917 | Berkey | .................... | 108/49 |
| 1,721,327 A * | 7/1929 | Anderson | ................... | 108/49 |
| 2,533,893 A * | 12/1950 | Nussbaum | ................... | 108/49 |
| 2,558,323 A * | 6/1951 | Strun | ....................... | 108/149 |
| 2,692,806 A * | 10/1954 | Grace | .................... | 108/49 |
| 2,703,265 A * | 3/1955 | Wolfe | .................... | 108/49 |
| 2,710,051 A * | 6/1955 | Greenberg | ................... | 108/49 |
| 2,988,310 A * | 6/1961 | Wright | ...................... | 108/49 |
| 3,680,158 A * | 8/1972 | Speed | .................... | 108/49 |
| 4,059,248 A * | 11/1977 | Kuntz | ...................... | 248/214 |
| 5,647,075 A * | 7/1997 | Perkins | ...................... | 108/49 |
| 8,025,015 B1* | 9/2011 | Kennedy, Sr. | ................... | 108/49 |
| 8,667,906 B2* | 3/2014 | Anglavis | ....................... | 108/141 |
| 2010/0187387 A1* | 7/2010 | Mitchell | .................. | 248/206.5 |
| 2010/0237206 A1* | 9/2010 | Barker | ...................... | 248/206.5 |
| 2010/0289288 A1* | 11/2010 | Smith et al. | ................ | 248/206.5 |
| 2011/0303808 A1* | 12/2011 | Bileth | ....................... | 248/206.5 |
| 2013/0186310 A1* | 7/2013 | Lymberis | ...................... | 108/152 |

\* cited by examiner

*Primary Examiner* — Jose V Chen
(74) *Attorney, Agent, or Firm* — Edward P. Dutkiewicz

(57) ABSTRACT

A portable and adjustable tattoo work station, comprising several components, in combination. There is a work platform which has a recess therein. There is a work platform connector and a shaft. The work platform connector couples the work platform and the shaft. There is a clamp coupled to the shaft. Lastly, there is a magnetic positive recess plug, which is coupled to the clamp.

14 Claims, 5 Drawing Sheets

ADJUSTABLE TATTOO TABLE

RULE 1.78(F) (1) DISCLOSURE

The Applicant has not submitted a related pending or patented non-provisional application within two months of the filing date of this present application. The invention is made by a single inventor, so there are no other inventors to be disclosed. This application is not under assignment to any other person or entity at this time.

BACKGROUND OF THE INVENTION

1. Field of the Invention

The present invention relates to a Adjustable Tattoo Table and more particularly pertains to an Adjustable and Removable Tattoo Table.

2. Description of the Prior Art

The use of tattoo tables is known in the prior art. More specifically, tattoo tables previously devised and utilized for the purpose of allowing a tattoo artist to work from a surface are known to consist basically of familiar, expected, and obvious structural configurations, notwithstanding the designs encompassed by the prior art which have been developed for the fulfillment of stated objectives and requirements.

While the prior art devices fulfill their respective, particular objectives and requirements, the prior art does not describe an Adjustable Tattoo Table that allows a user to have an Adjustable and Removable Tattoo Table from which to work. The benefit of such a device is that it allows the user to isolate those items which the artist is using, without the possibility of cross contamination of color and needle inventory. The adjustability of the table also allows a user to adjust the table to a desirable and comfortable height and location relative to the tattoo site.

In this respect, the Adjustable Tattoo Table according to the present invention substantially departs from the conventional concepts and designs of the prior art, and in doing so provides an apparatus primarily developed for the purpose of providing an Adjustable and Removable Tattoo Table.

Therefore, it can be appreciated that there exists a continuing need for a new and improved Adjustable Tattoo Table which can be used for providing a user an Adjustable and Removable Tattoo Table, allowing the artist to work in a comfortable, efficient and safe manner. In this regard, the present invention substantially fulfills this need.

SUMMARY OF THE INVENTION

In view of the foregoing disadvantages inherent in the known types of tattoo tables now present in the prior art, the present invention provides an improved Adjustable Tattoo Table. As such, the general purpose of the present invention, which will be described subsequently in greater detail, is to provide a new and improved Adjustable Tattoo Table which has all the advantages of the prior art and none of the disadvantages.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another.

By adjacent to a structure is meant that the location is near the identified structure.

To attain this, the present invention essentially comprises a portable and adjustable tattoo work station, comprising several components, in combination.

There is a work platform. The work platform is fabricated of a rigid material. The work platform has a generally rectilinear configuration with a first length and a first width. The first length is greater than the first width.

The work platform has an upper work surface and a lower surface, with a thickness there between. The thickness forms a peripheral edge. The edge of the work platform has an arcuate recess therein. The upper work surface has a raised area, with the raised area running the peripheral edge of the work surface. The lower surface has a raised area, with the raised area having a pair of threaded studs protruding there from. The threaded studs each having an associated thumb nut.

There is a work platform connector. The work platform connector is fabricated of a rigid material. The work platform connector has a second length and a second width. The work platform connector second length is greater than the work platform connector second width.

The work platform connector has a platform end having, an extent forming a first end. The work platform connector has a shaft end, having an extent forming a second end. The work platform connector has an upper surface and a lower surface, with a thickness there between. The thickness of the work platform connector forms a peripheral edge of the work platform connector.

The platform end of the work platform connector has a pair of stud holes there through. The stud holes are sized to receive and mate with the threaded studs of the lower surface of the work platform. The shaft end of the work platform connector has a shaft hole there through. The shaft hole runs from the upper surface of the work platform connector to the lower surface of the work platform connector. The shaft hole has a slot running along part of the length of the work platform connector. The extent of the work platform connector shaft end has a compression hole there through. The compression hole is oriented in an intersecting plane with the shaft hole of the work platform connector. The compression hole has a threaded portion and a smooth portion. The compression hole has an associated compression screw. The compression screw has a grip attached thereto.

There is a shaft. The shaft is fabricated of rigid material. The shaft has a generally solid round tubular configuration. The shaft has an upper end with an upper extent and a lower end with a lower extent. The shaft has a continuous outside diameter, with the outside diameter being sized to be received by and held by the shaft hole of the work platform connector. The shaft lower end extent has a generally curved protective bump pad. The bump pad is configured to prevent a user from striking the extent of the shaft lower end and sustaining an injury.

There is a clamp. The claim is fabricated of a rigid material. The claim has a generally C-shaped configuration. The clamp has an upper horizontal leg, a lower horizontal leg, and a vertical riser connecting the upper horizontal leg and the lower horizontal leg. The upper horizontal leg having a generally rectilinear configuration with an upper surface and a lower surface, with a thickness there between. The thickness forms a peripheral edge of the upper horizontal leg.

The lower horizontal leg has a generally rectilinear configuration with an upper surface, a lower surface, and a thickness there between. The thickness forms a peripheral edge of the upper horizontal leg. The lower horizontal leg has a threaded bolt hole there through, with the threaded bolt hole of the lower horizontal leg having an associated tightening bolt. The tightening bolt has a rotating pad on a threaded upper end. The tightening bolt has a lower end with a gripping portion.

The vertical riser has a generally rectilinear configuration with an upper end, having an extent, and a lower end, having an extent. The vertical riser has a length between the upper end and the lower end. The vertical riser also has a thickness, with the thickness forming a peripheral edge of the vertical riser. The vertical riser has an inner surface and an outer surface. The outer surface of the vertical riser has a rounded recess therein, with the recess having a pair of screw holes therein.

Lastly, there is a rounded recess plug. The rounded recess plug is fabricated of a magnetic positive material. The term "magnetic positive" means any metal or metal alloy or metallic material which allows a magnet to attach by means of a magnetic field. Iron would be a magnetic positive material, while aluminum would not be magnetic positive.

The rounded recess plug is sized to be received in, and mate with, the rounded recess of the vertical riser. The recess plug has a pair of screw holes there through. The screw holes of the recess plug each have an associated screw for securing the recess plug within the rounded recess of the vertical riser.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved Adjustable Tattoo Table which has all of the advantages of the prior art tattoo tables and none of the disadvantages.

It is another object of the present invention to provide a new and improved Adjustable Tattoo Table which may be easily and efficiently manufactured and marketed.

It is further object of the present invention to provide a new and improved Adjustable Tattoo Table which is of durable and reliable constructions.

An even further object of the present invention is to provide a new and improved Adjustable Tattoo Table which is susceptible of a low cost of manufacture with regard to both materials and labor, and which accordingly is then susceptible of low prices of sale to the consuming public, thereby making such Adjustable Tattoo Table economically available to the buying public.

Even still another object of the present invention is to provide a Adjustable Tattoo Table allow a tattoo artist to work in a comfortable, efficient, and safe manner.

Lastly, it is an object of the present invention to provide a new and improved portable and adjustable tattoo work station, comprising several components, in combination. There is a work platform which has a recess therein. There is a work platform connector and a shaft. The work platform connector couples the work platform and the shaft. There is a clamp coupled to the shaft. Lastly, there is a magnetic positive recess plug, which is coupled to the clamp.

It should be understood that while the above-stated objects are goals which are sought to be achieved, such objects should not be construed as limiting or diminishing the scope of the claims herein made.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
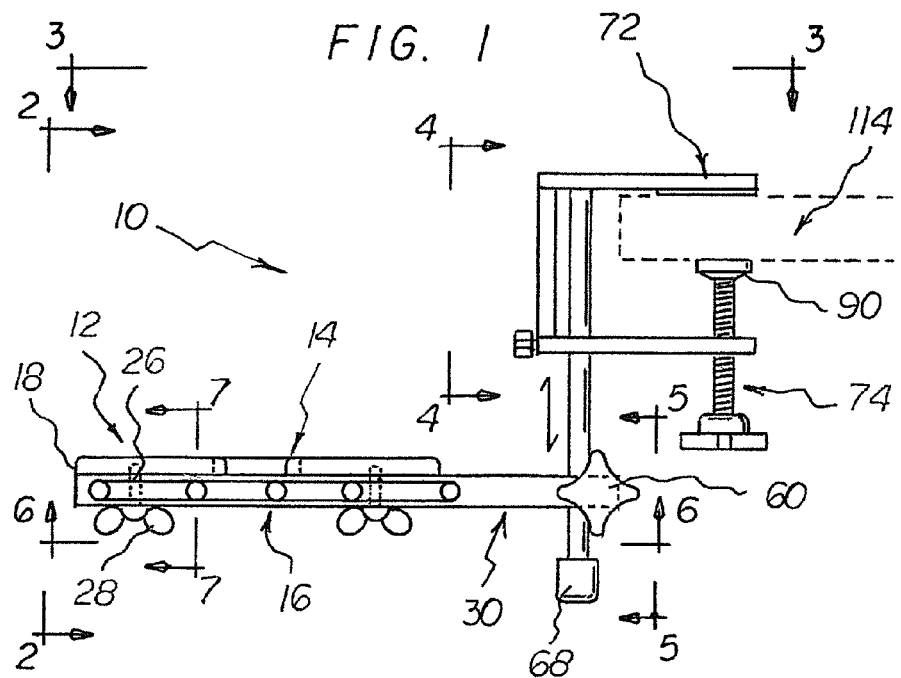
FIG. 1 is a side elevational view of the adjustable and removable tattoo table.
Figure 2:
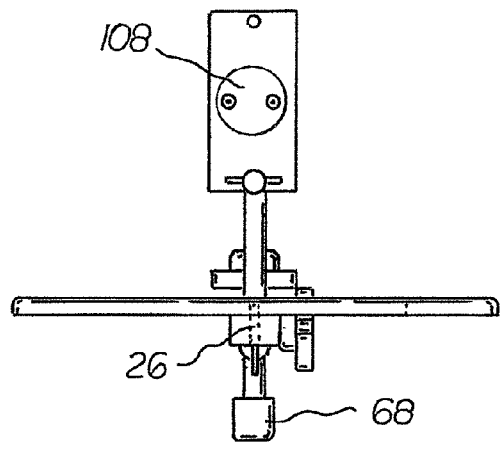
FIG. 2 is a view taken along line 2-2 of FIG. 1.
Figure 3:
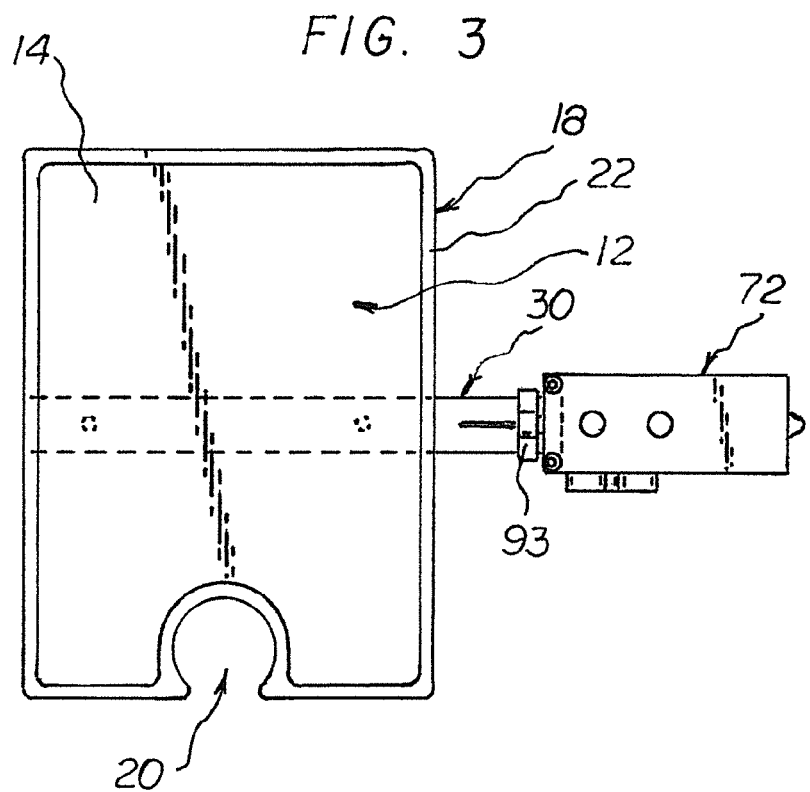
FIG. 3 is a view taken along line 3-3 of FIG. 1.
Figure 4:
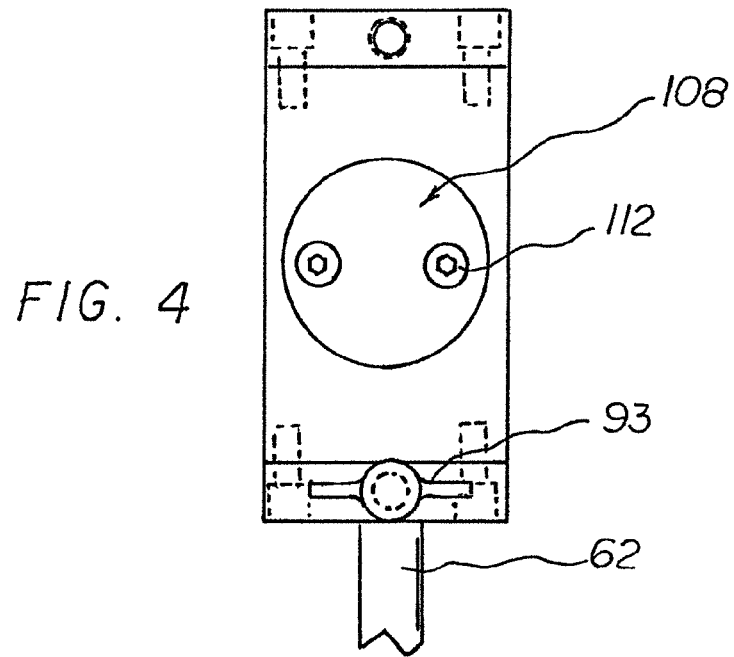
FIG. 4 is a view taken along line 4-4 of FIG. 1.
Figure 5:
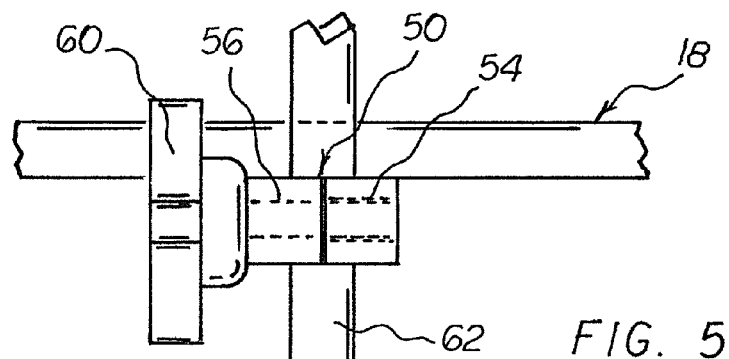
FIG. 5 is a view taken along line 5-5 of FIG. 1.
Figure 6:
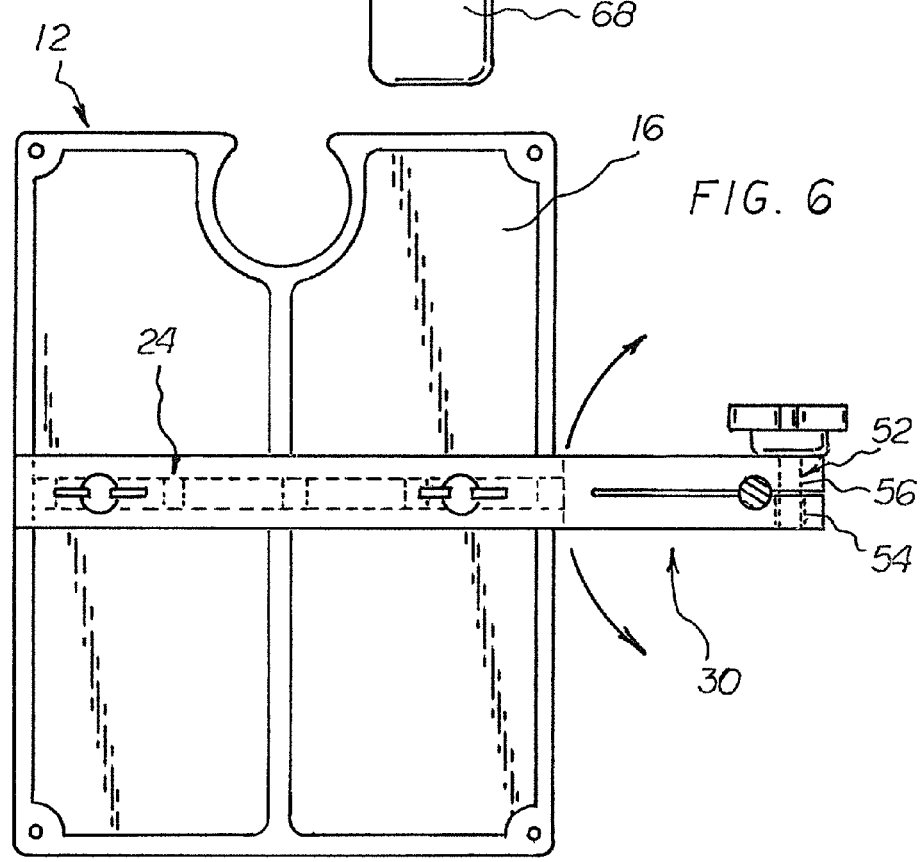
FIG. 6 is a view taken along line 6-6 of FIG. 1.
Figure 7:
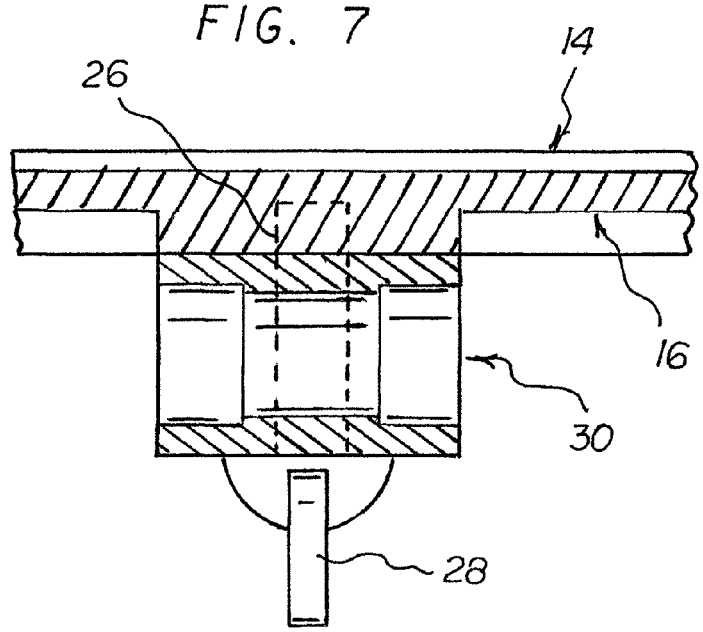
FIG. 7 is a view taken along line 7-7 of FIG. 1.
Figure 8:
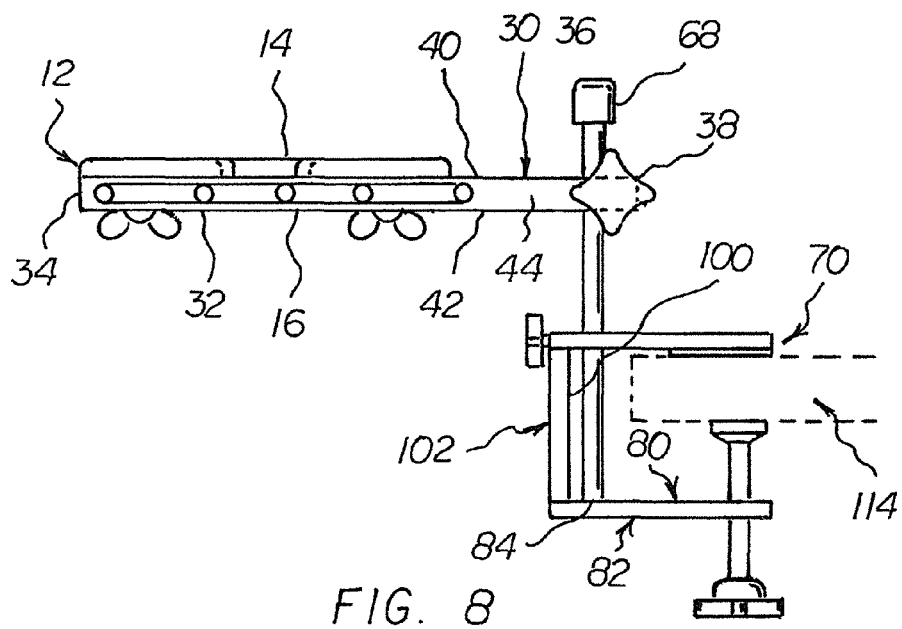
FIG. 8 is a side elevational view showing the tattoo table position relative to the clamp to be different than that of FIG. 1. This indicates that the table is height adjustable relative to the clamp.
Figure 9:
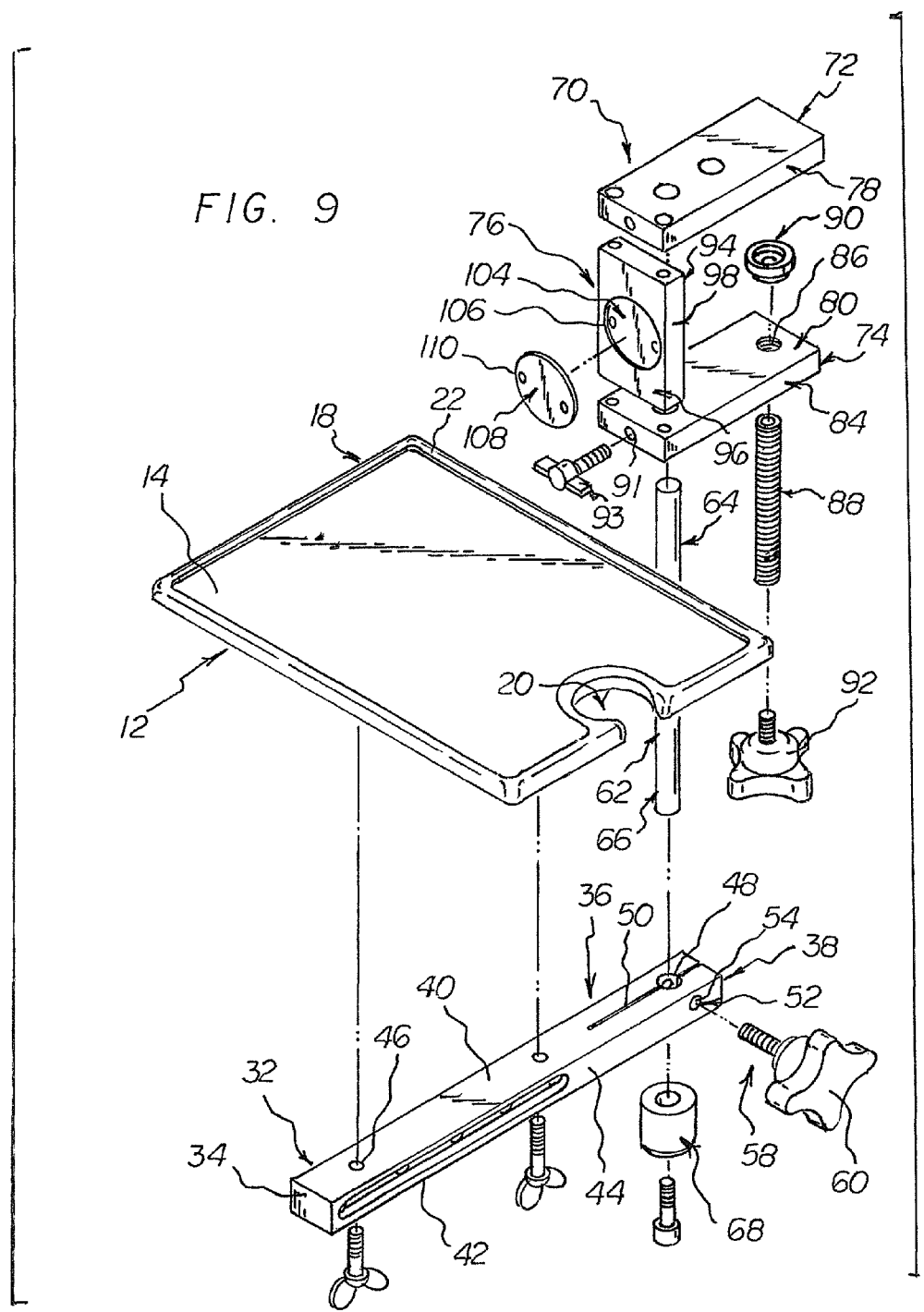
FIG. 9 is a bracketed exploded view of the tattoo table, showing the components and their relationships to each other.

With reference now to the drawings, and in particular to FIG. 1 thereof, the preferred embodiment of the new and improved Adjustable Tattoo Table embodying the principles and concepts of the present invention and generally designated by the reference numeral 10 will be described.

The present invention, the Adjustable Tattoo Table 10 is comprised of a plurality of components. Such components in their broadest context include a work platform, a work platform connector, a shaft and a clamp. Such components are individually configured and correlated with respect to each other so as to attain the desired objective.

A portable and adjustable tattoo work station 10, comprising several components, in combination, is herein described.

There is a work platform 12. The work platform is fabricated of a rigid material. The work platform has a generally rectilinear configuration with a first length and a first width. The first length is greater than the first width.

The work platform has an upper work surface 14 and a lower surface 16, with a thickness there between. The thickness forms a peripheral edge 18. The edge of the work platform has an arcuate recess 20 therein. The upper work surface has a raised area 22, with the raised area running the peripheral edge of the work surface. The lower surface has a raised area 24, with the raised area having a pair of threaded studs 26 protruding there from. The threaded studs each having an associated thumb nut 28.

There is a work platform connector 30. The work platform connector is fabricated of a rigid material. The work platform connector has a second length and a second width. The work platform connector second length is greater than the work platform connector second width.

The work platform connector has a platform end 32 having, an extent forming a first end 34. The work platform connector has a shaft end 36, having an extent forming a second end 38. The work platform connector has an upper surface 40 and a lower surface 42, with a thickness there between. The thickness of the work platform connector forms a peripheral edge 44 of the work platform connector.

The platform end of the work platform connector has a pair of stud holes 46 there through. The stud holes are sized to receive and mate with the threaded studs of the lower surface of the work platform. The shaft end of the work platform connector has a shaft hole 48 there through. The shaft hole runs from the upper surface of the work platform connector to the lower surface of the work platform connector. The shaft hole has a slot 50 running along part of the length of the work platform connector. The extent of the work platform connector shaft end has a compression hole 52 there through. The compression hole is oriented in an intersecting plane with the shaft hole of the work platform connector. The compression hole has a threaded portion 54 and a smooth portion 56. The compression hole has an associated compression screw 58. The compression screw has a grip 60 attached thereto.

There is a shaft 62. The shaft is fabricated of rigid material. The shaft has a generally solid round tubular configuration. The shaft has an upper end 64 with an upper extent and a lower end 66 with a lower extent. The shaft has a continuous outside diameter, with the outside diameter being sized to be received by and held by the shaft hole of the work platform connector. The shaft lower end extent has a generally curved protective bump pad 68. The bump pad is configured to prevent a user from striking the extent of the shaft lower end and sustaining an injury.

There is a clamp 70. The claim is fabricated of a rigid material. The claim has a generally C-shaped configuration. The clamp has an upper horizontal leg 72, a lower horizontal leg 74, and a vertical riser 76 connecting the upper horizontal leg and the lower horizontal leg. The upper horizontal leg having a generally rectilinear configuration with an upper surface and a lower surface, with a thickness there between. The thickness forms a peripheral edge 78 of the upper horizontal leg, a peripheral edge of the lower horizontal leg 80.

The lower horizontal leg has a generally rectilinear configuration with an upper surface 80, a lower surface 82, and a thickness there between. The thickness forms a peripheral edge 84 of the upper horizontal leg. The lower horizontal leg has a threaded bolt hole 86 there through, with the threaded bolt hole of the lower horizontal leg having an associated tightening bolt 88. The tightening bolt has a rotating pad 90 on a threaded upper end. The tightening bolt has a lower end with a gripping portion 92.

The lower horizontal leg has a threaded end locking bolt hole 91 therein, with an associated locking bolt 93 for fastening the shaft in position and holding the clamp to the shaft.

The vertical riser has a generally rectilinear configuration with an upper end 94, having an extent, and a lower end 96, having an extent. The vertical riser has a length between the upper end and the lower end. The vertical riser also has a thickness, with the thickness forming a peripheral edge 98 of the vertical riser. The vertical riser has an inner surface 100 and an outer surface 102. The outer surface of the vertical riser has a rounded recess 104 therein, with the recess having a pair of screw holes 106 therein.

Lastly, there is a rounded recess plug 108. The rounded recess plug is fabricated of a magnetic positive material. The term "magnetic positive" means any metal or metal alloy or metallic material which allows a magnet to attach by means of a magnetic field. Iron would be a magnetic positive material, while aluminum would not be magnetic positive.

The rounded recess plug is sized to be received in, and mate with, the rounded recess of the vertical riser. The recess plug has a pair of screw holes 110 there through. The screw holes of the recess plug each have an associated screw 112 for securing the recess plug within the rounded recess of the vertical riser. The clamp holds the portable and adjustable tattoo work station in position on an existing table top 114.

The rounded recess plug is a sheet of magnetic positive material. In the preferred embodiment, the sheet is rounded, though in variations the recess plug may be any shape, including any irregular or undefined shape. The general description of the rounded recess plug is then a "sheet".

In the tattoo industry and practice, tattoo artists work from a surface, which is usually a table or counter top. There, the artists stores the number of colors and supplies he or she will use to tattoo a customer. Generally, the artist pours small amounts of colored ink into small cups, for use in creating the tattoo. If there individual cups are on the same surface as the larger bottle, there exists a possibility of cross contamination.

The adjustable and removable tattoo table is used in the following manner. The tattoo table is clamped to an existing table or countertop. This creates a separate work surface. The adjustable tattoo table may then be covered with a sheet of impervious material, such as a sheet of plastic or other impenetrable barrier. The artists then sets up the number of ink cups the artist will use, along with any other supplies on the barrier material. There is a recess in the work platform for holding a washing cup, which is used to wash the needle tip when changing colors. The magnetic positive plug which is set into the side of the clamp provides a location where the needle drive motor may be magnetically attached, removing the drive from the surface which holds the inventory of colored inks. This allows the artist to work from an isolated area. When the tattoo is complete, the needle is appropriately disposed, the motor is removed from the clamp, and the plastic barrier is folded and removed from the stand, leaving a clean work station with limited movement and cleanup.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accord-

What is claimed as being new and desired to be protected by Letters Patent of the United States is as follows:

1. A portable and adjustable tattoo work station, comprising, in combination:
 a work platform a first length and a first width, the work platform having an upper work surface and a lower surface with a thickness there between, the thickness forming a peripheral edge;
 a work platform connector having a second length and a second width, the work platform connector having platform end having an extent forming a first end, the work platform connector having a shaft end having an extent forming a second end, the work platform connector shaft end having a shaft hole there through, the work platform connector having an upper surface and a lower surface and a thickness there between, the work platform connector being coupled to the work platform;
 a shaft having an upper end with an upper extent and the shaft having a lower end with a lower extent, the shaft being received by and held by the shaft hole of the work platform connector;
 a clamp having a generally C-shaped configuration, the clamp having an upper horizontal leg and a lower horizontal leg and a vertical riser connecting the upper horizontal leg and the lower horizontal leg, the upper horizontal leg having an upper surface and a lower surface and a thickness there between, the lower horizontal leg having an upper surface and a lower surface and a thickness there between, the vertical riser having an upper end having an extent and a lower end having an extent and a thickness there between, the vertical riser having an inner surface and an outer surface, the clamp being coupled to the work platform by the shaft; and
 a recess plug having a pair of screw holes there through, the screw holes of the recess plug each having an associated screw for coupling the recess plug to the clamp.

2. The portable and adjustable tattoo work station as described in claim 1, with the work station further comprising:
 the outer surface of the vertical riser having a recess therein, with the recess having a pair of screw holes therein; and
 the recess plug being fabricated of a magnetic positive material, the recess plug being located with the recess of the outer surface of the vertical riser.

3. The portable and adjustable tattoo work station as described in claim 2, with the work station further comprising:
 the work platform lower surface having a raised area with the raised area having a pair of threaded studs protruding there from, the threaded studs each having an associated thumb nut; and
 the work platform thickness forming a peripheral edge of the work platform connector.

4. The portable and adjustable tattoo work station as described in claim 3, with the work station further comprising the peripheral edge of the work platform having a recess therein.

5. The portable and adjustable tattoo work station as described in claim 4, with the work station further comprising:
 the work platform first length being greater than the work platform first width;
 the work platform connector second length being greater than the work platform connector second width;
 the shaft having a generally solid round tubular configuration; and
 the recess plug having a pair of screw holes there through, with the screw holes of the recess plug each having an associated screw for securing the recess plug within the recess of the vertical riser.

6. The portable and adjustable tattoo work station as described in claim 5, with the work station further comprising:
 the work platform upper work surface having a raised area running the peripheral edge of the work surface;
 the platform end of the work platform connector having a pair of stud holes there through, the stud holes being sized to receive and mate with the threaded studs of the lower surface of the work platform;
 the shaft end of the work platform connector having a shaft hole there through;
 the shaft having a continuous outside diameter with the outside diameter being sized to be received by and held by the shaft hole of the work platform connector;
 the recess of the vertical riser being generally rounded; and
 the recess plug having a generally rounded configuration.

7. The portable and adjustable tattoo work station as described in claim 6, with the work station further comprising:
 the work platform connector shaft hole located on the shaft end of the work platform connector running from the upper surface of the work platform connector to the lower surface of the work platform connector;
 the lower horizontal leg of the clamp having a threaded bolt hole there through; and
 the recess plug being sized to be received in and mate with the generally rounded recess of the vertical riser.

8. The portable and adjustable tattoo work station as described in claim 7, with the work station further comprising:
 the work platform having a generally rectilinear configuration
 the work platform connector shaft hole having a slot running from the extent of the shaft end along part of the length of the work platform connector; and
 the threaded bolt hole of the lower horizontal leg of the clamp having an associated tightening bolt.

9. The portable and adjustable tattoo work station as described in claim 8, with the work station further comprising:
 the extent of the work platform connector shaft end having a compression hole there through;
 the clamp upper horizontal leg having a generally rectilinear configuration;
 the clamp lower horizontal leg having a generally rectilinear configuration;
 the tightening bolt of the lower horizontal leg of the clamp having a rotating pad coupled to a threaded upper end and the tightening bolt having a lower end with a gripping portion;
 the vertical riser of the clamp having a generally rectilinear configuration; and
 the work platform recess has an arcuate configuration.

10. The portable and adjustable tattoo work station as described in claim 9, with the work station further comprising:
 the compression hole being oriented at a right angle to the shaft hole;
 the shaft lower end extent having a generally curved protective bump pad, the bump pad being configured to prevent a user from striking the extent of the shaft lower end and sustaining an injury;
 the thickness of the upper horizontal leg of the clamp forming a peripheral edge of the upper horizontal leg of the clamp;

the thickness of the lower horizontal leg of the clamp forming a peripheral edge of the lower horizontal leg; and the thickness of the vertical riser of the clamp forming a peripheral edge of the vertical riser.

11. The portable and adjustable tattoo work station as described in claim 10, with the work station further comprising the compression hole having a threaded portion and a smooth portion, the compression hole having an associated compression screw, the compression screw having a grip attached thereto.

12. The portable and adjustable tattoo work station as described in claim 11, with the work station further comprising:

the work platform being fabricated of a rigid material;

the work platform connector being fabricated of a rigid material;

the shaft being fabricated of rigid material; and the clamp being fabricated of a rigid material.

13. A portable and adjustable tattoo work station, comprising, in combination:

a work platform having an upper work surface and a lower surface with a peripheral edge;

a work platform connector having platform end and a shaft end with the shaft end of the work platform connector having a shaft hole there through, the work platform connector being coupled to the work platform;

a shaft having an upper end and a lower end, the shaft being received by and held by the shaft hole of the work platform connector, a clamp coupled to the work platform by the shaft; and a sheet of a magnetic positive material having screw holes there through, the screw holes of the sheet of magnetic positive material each having an associated screw for securing the sheet of magnetic positive material to the clamp.

14. The portable and adjustable tattoo work station as described in claim 13, with the work station further comprising the shaft hole having a slot there through, the shaft end slot having a compression hole there through with the compression hole having a threaded portion and a smooth portion, the compression hole having an associated compression screw, the compression screw having a grip attached thereto, the compression hole having a threaded portion and a smooth portion, the compression hole having an associated compression screw.

* * * * *